United States Patent
Palasis et al.

(10) Patent No.: US 6,984,411 B2
(45) Date of Patent: Jan. 10, 2006

(54) METHOD FOR ROLL COATING MULTIPLE STENTS

(75) Inventors: Maria Palasis, Wellesley, MA (US); Wendy Naimark, Cambridge, MA (US); Tim Mickley, Elk River, MN (US); Toby Freyman, Watertown, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 10/684,131

(22) Filed: Oct. 14, 2003

(65) Prior Publication Data

US 2005/0079274 A1 Apr. 14, 2005

(51) Int. Cl.
*B05D 1/02* (2006.01)

(52) U.S. Cl. .................... 427/2.24; 427/2.25; 427/2.28; 427/425; 427/434.2

(58) Field of Classification Search ................. 427/2.1, 427/2.24, 2.28, 421, 425, 430.1, 428, 434.2, 427/2.25
See application file for complete search history.

(56) References Cited

U.S. PATENT DOCUMENTS

| | | | | |
|---|---|---|---|---|
| 5,534,287 A | * | 7/1996 | Lukic | 427/2.25 |
| 5,620,738 A | * | 4/1997 | Fan et al. | 427/2.3 |
| 6,284,305 B1 | * | 9/2001 | Ding et al. | 427/2.28 |
| 6,554,942 B2 | * | 4/2003 | Solar et al. | 156/244.11 |
| 6,730,349 B2 | * | 5/2004 | Schwarz et al. | 427/2.1 |
| 6,743,462 B1 | * | 6/2004 | Pacetti | 427/2.24 |
| 2002/0127327 A1 | | 9/2002 | Schwarz et al. | |

* cited by examiner

*Primary Examiner*—Bret Chen
(74) *Attorney, Agent, or Firm*—Kenyon & Kenyon

(57) ABSTRACT

An improved method for high-volume production of coated stents with highly uniform stent coatings using a roll coating technique is provided. In a first embodiment, uncoated stents are placed onto rotating stent holders with automated stent handling equipment. The holders are mounted on an endless conveyer belt which advances the stents toward a stent coater. As the stents advance through the coater, the holders rotate, thereby rolling the stents about their longitudinal axes as coating material is sprayed toward them, ensuring the stents are uniformly coated on their exterior and interior surfaces. After the conveyer turns to carry the coated stents back toward the loading area, the rotating stents pass again through the coating spray, downstream of the initial coating location, thereby increasing the efficient utilization of the coating material. The conveyer then advances the coated stents to an unloading area for removal before the holders return to the stent loading area to receive new stents.

21 Claims, 4 Drawing Sheets

METHOD FOR ROLL COATING MULTIPLE STENTS

FIELD OF THE INVENTION

The present invention generally regards the holding of stents during manufacture to enable the application of therapeutic and/or protective coatings. More specifically, the present invention pertains to a method for high-throughput, efficient and uniform coating of stents, wherein the stents placed on rotating fixtures on a conveyer, and the conveyer passes the rotating stents through a coating spray or immersion bath to apply a coating to the stents.

BACKGROUND

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location.

The delivery of expandable stents is a specific example of a medical procedure that involves the deployment of coated implants. Expandable stents are tube-like medical devices, typically made from stainless steel, Tantalum, Platinum or Nitinol alloys, designed to be placed within the inner walls of a lumen within the body of a patient. These stents are typically maneuvered to a desired location within a lumen of the patient's body and then expanded to provide internal support for the lumen. The stents may be self-expanding or, alternatively, may require external forces to expand them, such as by inflating a balloon attached to the distal end of the stent delivery catheter.

Because of the direct contact of the stent with the inner walls of the lumen, stents have been coated with various compounds and therapeutic agents to enhance their effectiveness. These coatings may, among other things, be designed to facilitate the acceptance of the stent into its applied surroundings. Such coatings may also be designed to facilitate the delivery of one of the foregoing therapeutic agents to the target site for treating, preventing, or otherwise affecting the course of a disease or tissue or organ dysfunction.

Where the stent has been coated, care must be taken during its manufacture and delivery within the patient to ensure the coating is evenly applied and firmly adherent to the stent, and further that the coating is not damaged or completely removed from the implant during the deployment process. When the amount of coating is depleted the implant's effectiveness may be compromised and additional risks may be inured into the procedure. For example, when the coating of the implant includes a therapeutic, if some of the coating were removed during deployment, the therapeutic may no longer be able to be administered to the target site in a uniform and homogenous manner. Thus, some areas of the target site may receive high quantities of therapeutic while others may receive low quantities of therapeutic. Similarly, if the therapeutic is ripped from the implant it can reduce or slow down the blood flowing past it, thereby, increasing the threat of thrombosis or, if it becomes dislodged, the risk of embolisms. In certain circumstances, the removal and reinsertion of the stent through a second medical procedure may be required where the coatings have been damaged or are defective.

The mechanical process of applying a coating onto a stent may be accomplished in a variety of ways, including, for example, the spraying of the coating substance onto the stent and so-called spin-dipping, i.e., dipping a spinning stent into a coating solution to achieve the desired coating. Common to these processes is the need to apply the coating in a uniform manner to ensure an intact, robust coating of the desired thickness is formed on the stent. In order to achieve the desired uniform and complete coating, it has been common for the stents to be handled individually, with each stent separately loaded onto a stent holder and the coating applied to the stent before the next stent is coated. This individual handling typically has resulted in low production rates of coated stents. A further disadvantage of these prior stent coating processes is that, because the stents are wire mesh structures with substantial void area between the mesh wires, the utilization of the stent coating material sprayed toward the stents is very low. For example, in some cases the amount of stent coating sprayed toward the stent which actually adheres to the stent mesh is less than five percent.

Thus, there is a need for a method for coating stents which efficiently applies the stent coating material in a manner that results in a high quality, uniform coating on the stents at high coated stent production rates.

SUMMARY OF THE INVENTION

The present invention is directed to a method for overcoming the foregoing disadvantages. Specifically, in a first step of a first embodiment of the method, stents are loaded with high speed stent handling equipment onto rotating pins that are mounted to an endless conveyer belt. In a second step, while the stents are rolling about their longitudinal axes atop the rotating pins, stent coating material is applied as the endless belt advances the stents through a stent coater containing a coating sprayer. As the stents are returned toward the stent loading area by the endless belt, they receive additional coating material from the coating sprayer as they pass a second time through the coating spray downstream of the initial coating location. The coated stents are then removed from their holders before the endless belt returns the stent holders to the stent loading area to receive new uncoated stents.

A number of alternative embodiments for performance of the method of the present invention are envisioned. For example, there may be a number of alternative embodiments for performing the stent placement step, such as providing stents pre-mounted on stent holders with rotating pins equipping with corresponding stent holder receivers to facilitate stent handling by automated stent placement equipment. Similarly, in the step of applying the coating material, rather than spraying the coating material perpendicularly across the endless belt, the coating may be applied from a sprayer aligned with the major axis of the endless belt such that the rolling stents have a longer exposure to the coating spray. The sprayer may also apply the coating while the spray head is rotating about the line of rolling stents. In a further embodiment, the coating application step may be performed by drawing the rolling stents through a coating bath. Other embodiments extend the stent coating step to include the endless belt reversing direction several times to cause the rolling stents to pass several times through the downstream portions of the coating spray to improve coating material utilization, and the inclusion of additional stent processing steps between the coating application step and the coated stent unloading step, such as accelerating the drying of the stent coating by advancing the coated stents through an infrared coating dryer.

The result of the various foregoing embodiments of the method of the present invention is high volume, efficient and lower-cost production of stents with a highly uniform coating on their exterior and, in desired, interior surfaces.

DETAILED DESCRIPTION

Figure 1:
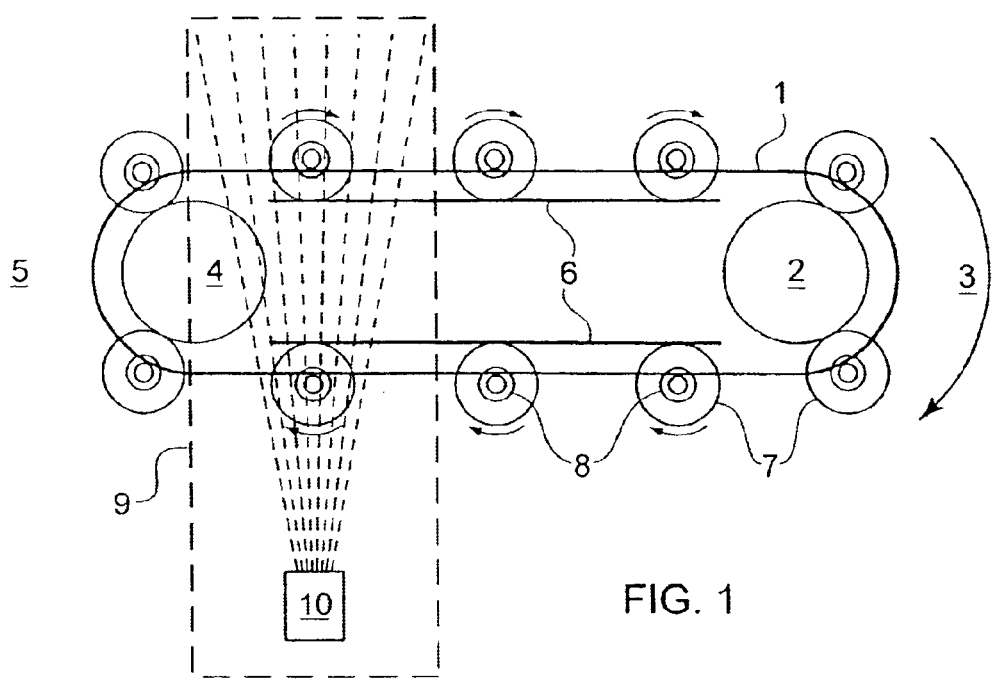
FIG. 1 is a schematic overhead view of a stent coating process in accordance with an embodiment of the method the present invention.

The present invention is directed to a method for overcoming the foregoing disadvantages by applying a stent coating to stents that are being rolled about their longitudinal axis, where the stents are loaded onto rotating holders affixed to a conveyer, and the conveyer carries the rotating stents and holders through a coating applicator one or more times.

The method of the present invention in a first embodiment is as follows. In this first embodiment, a conveyer in the form of an endless belt 1 is arranged around a first pulley 2 at a first end 3 of the belt and a second pulley 4 at a second, opposite end 5 of the belt. Endless belt 1 may be advanced by rotating either pulley 2 or pulley 4. Backing plates 6 are provided in the region between pulleys 2 and 4. The backing plates, which can be located adjacent to either the inner or outer face of the belt, are arranged to contact outer peripheral edges of rotating pins 7 mounted on endless belt 1 (details of rotating pins 7 and their mounting are discussed further, below). When endless belt 1 is advanced, the friction between the outer peripheral portions of rotating pins 7 and backing plates 6 causes the pins to rotate.

As a first step of the method in this embodiment, stents 8 are placed with automated stent placement equipment (not illustrated) onto rotating pins 7 as endless belt 1 is advanced. In this embodiment, the stents are loaded onto the rotating pins near the first end 3 of the endless belt, and advance toward second end 5 as endless belt 1 advances. In FIG. 1, the freshly loaded, uncoated stents are on endless belt 1 on the lower side of the illustration, moving from first end 3 toward second end 5. At a location along endless belt 1 separate from the stent loading location, a stent coater 9 is positioned such that it dispenses a stent coating spray toward endless belt 1 when activated. In this embodiment, stent coater 9 includes a stent coating sprayer 10 located near second end 5 which sprays the coating material generally perpendicularly across endless belt 1. The stent coater may further include a housing (not illustrated) to contain and potentially reclaim coating overspray.

In the second step of the method in this first embodiment, endless belt 1 is advanced to cause stents 8 to roll about their longitudinal axes as their respective pins 7 rotate (due to the pins' frictional engagement with backing plate 6). As endless belt 1 advances, the rolling stents 8 are simultaneously carried along the path of endless belt 1 into and out of the stent coater. The step of applying the stent coating to the stents is performed by causing coating sprayer 10 to dispense the stent coating onto stents 8 as they pass through the stent coater. Further, because endless belt 1 reverses direction at pulley 4, stent coating spray that passes by or through the stents moving toward second end 5 can be utilized to apply additional coating material to the stents as they pass from second end 5 back toward first end 3, thereby substantially improving the efficiency of the coating process. Finally, as the coated stents 8 approach first end 3, they are removed from their respective rotating pins 7 by automated stent removal equipment (not illustrated), prior to the rotating pins' return to the stent loading area for loading of new uncoated stents.

Figure 2:
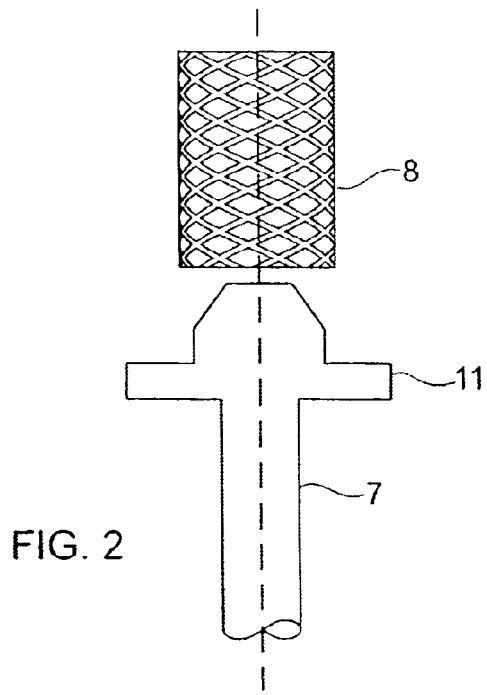
FIG. 2 is a side view showing a stent and the upper portion of a rotating pin on which the stent is placed in accordance with the method of the present invention.

The rotating pins 7 in this embodiment, and their relationship to endless belt 1, backing plates 6 and stents 8, arc now further described. FIG. 2 illustrates a schematic view of the upper portion of a rotating pin 7 and its relationship to stent 8. When placed onto rotating pin 7, stent 8 is oriented with its longitudinal axis generally in line with the longitudinal axis of a rotating pin 7. Rotating pin 7 is sized such that when stent 8 is placed over the top of pin 7, the stent is supported by pin 7 in a manner which ensures that stent 8 rotates with pin 7 when the pin is rotated around its longitudinal axis. In this embodiment, rotating pin 7 has a radial extension or shelf 11 upon which stent 8 rests when placed over the top of pin 7. Alternatively, rotating pin 7 may have a tapered shape, such that the inner diameter of stent 8 rests directly upon the tapered sides of pin 7. Rotating pin 7 is preferably configured such that its protrusion into the interior annular region of stent 8, while sufficient to ensure stent 8 is retained on the pin during its transit through stent coating applicator 9, is minimized in order to minimize the extent to which pin 7 interferes with the application of the coating spray to the inner surface of stent 8.

Figure 3A:
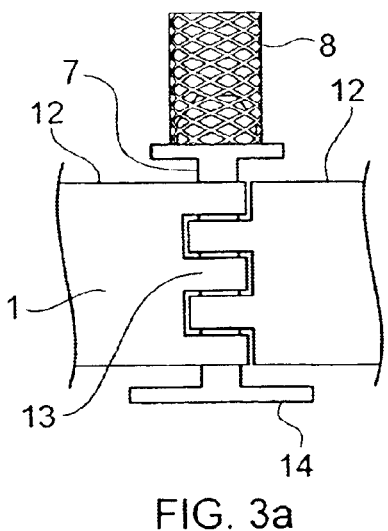
FIG. 3 is a side illustration of stent-bearing rotating pins mounted on a conveyer belt in accordance with the method of the present invention.
Figure 3B:
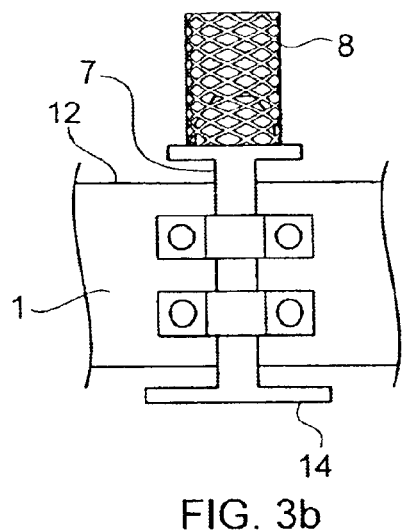

FIG. 3 shows the general arrangement of rotating pins 7 and stents 8 on endless belt 1 in the first embodiment. In both FIG. 3a and FIG. 3b, stents 8 rest on the tops of rotating pins 7, which are in turn rotably held on belt 1. Any of a variety of conveyer arrangements well known in the art may be used to rotably hold pins 7. In this embodiment, the pins are held by belt links 12 of endless belt 1. The belt links 12 may be arranged any suitable manner that permits the pins 7 to rotate about their longitudinal axes as the belt advances, such as with interlocking fingers or hooks 13 on the ends of the links which cooperate with the pins 7 and an adjacent link to effectively use rotating pins 7 as hinge pins in the endless belt, as illustrated in FIG. 3a. Alternatively, endless belt 1 may be an endless rubber belt to which are mounted U-shaped brackets which loosely capture rotating pins 7 between the belt and the brackets, as illustrated in FIG. 3b.

Figure 4:
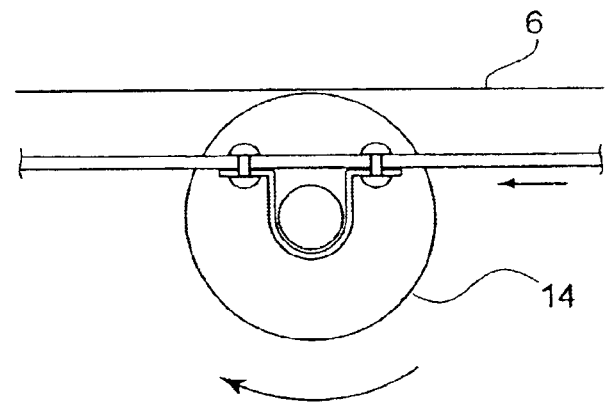
FIG. 4 is an overhead view of the stent-bearing rotating pins and conveyer belt shown in FIG. 3 in accordance with the method of the present invention.

In order to provide for the rotation of rotating pins 7 as endless belt 1 advances, a flange 14 is provided in this embodiment on each rotating pin 7. As shown in the overhead view in FIG. 4, flange 14 is of sufficient radius that its outer periphery is in rolling contact with backing plates 6 as endless belt 1 advances, thereby causing pins 7 and their respective, stents 8 to roll about their longitudinal axes as belt 1 advances. Flange 14 may be provided above, below, or in a gap through, endless belt 1, as desired to provide positive engagement of flanges 14 against backing plates 6. As those of skill in the art will readily recognize, a variety of alternative means other than backing plates 6 may be provided to cause rotating pins 7 to roll stents 8, such as gear-drive of the rotating pins, so as long as the desired rotation of stents 8 is obtained. Alternatively, rotating pins 7 may be rotated by means that are independent of the means that advance endless belt, for example, by a separate electric motor.

The diameter of flange 14 and the speed of advance of endless belt 1 are adjusted as necessary to ensure an optimal stent coating is obtained. This requires stents 8 to be rotated at a rate that is slow enough to ensure effective coverage of outer and inner portions of stent 8 by sprayer 10 as the stents traverse through the coating spray, but fast enough to ensure that the stents make at least one complete revolution while stent 8 is within the spray pattern from sprayer 10. An endless belt advance speed of 0.1–0 cm per second and a stent rotation rate of 10–100 degrees per second may be used to obtain satisfactory coating of stents with the foregoing roll coating method.

Figure 5:
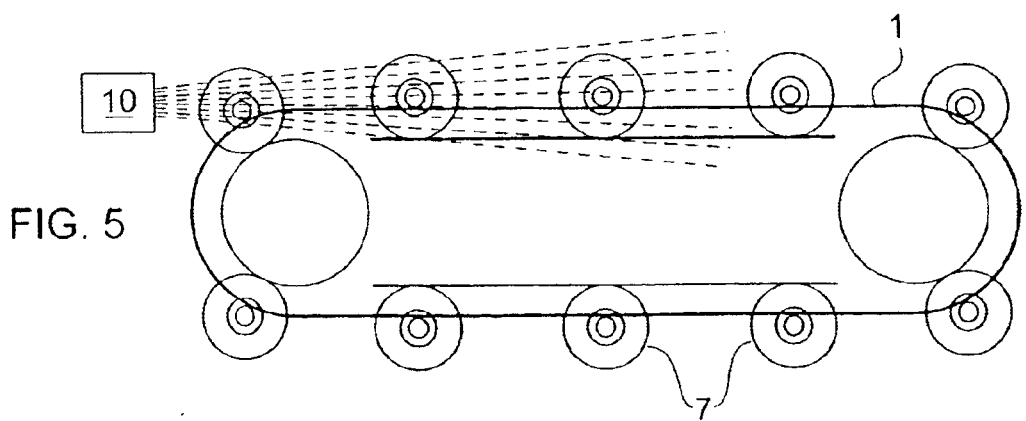
FIG. 5 is a schematic overhead view of the stent-bearing rotating pins and conveyer belt shown in FIG. 3 illustrating an alternative approach for the step of applying the stent coating in accordance with the method of the present invention.

In addition to executing the step of applying the coating to the stents 8 using a spray applicator aligned perpendicular to the direction of advance of endless belt 1, a number of alternative spray configurations can be envisioned. For example, in order to minimize the interference of rotating pins 7 with the application of the coating to the inner surface of stents 8, coating sprayer 10 may be elevated above endless belt 1 and aligned to dispense the coating spray downward at an angle toward the rolling stents 8. As shown in FIG. 5, coating sprayer 10 could also be located above endless belt 1 and aligned with the belt such that it sprays in the direction of stent travel and thus has an extended opportunity to apply the coating to the stents. In a further alternative sprayer embodiment, the coating sprayer may be provided on means such as a rotating arm that permits the sprayer to rotate around the rolling stents as they are advanced on the conveyer. Performing the coating application step in this embodiment provides further assurance a uniform coating will be obtained at high coated stent production levels.

An additional embodiment of the present method includes multiple direction reversals of endless belt 1 downstream of coating sprayer 10 such that stents 8 re-enter the spray dispensed from sprayer 10 several times before belt 1 returns to a stent removal station. By expanding the coating application step in this manner, this embodiment provides for enhanced coating efficiency as each pass of stents 8 through the downstream portions of the coating spray further improves the utilization of the sprayed coating and thereby improves coating efficiency.

A further advantage of the foregoing method is that after the step of applying the coating to the rolling stents, there may be provided additional steps which enhance high volume coated stent production. An exemplary further embodiment of the present method thus may include the step of passing the stents through a coating dryer (such as an infrared heater) following the application of the coating, wherein the rolling stents present all their coated surfaces to the dryer for even, accelerated drying prior to removal from their respective rotating pins 7. Alternatively, the conveyer and/or the stent holder may be heated to accelerate coating drying rates before the stents are removed from the conveyer.

Figure 6A:
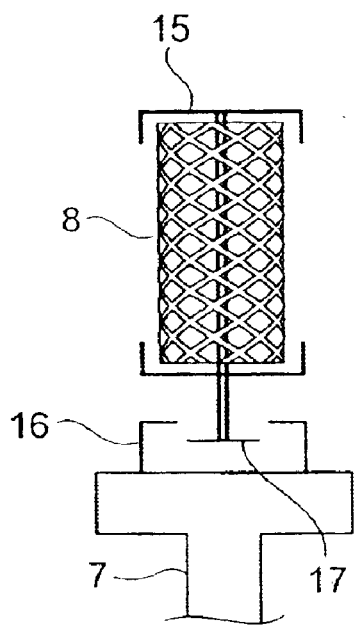
FIG. 6 are schematic side views of alternative stent holders and rotating pin mounts for engaging and holding stent holders for performing the step of placing the stents on the conveyer in accordance with the method of the present invention.
Figure 6B:
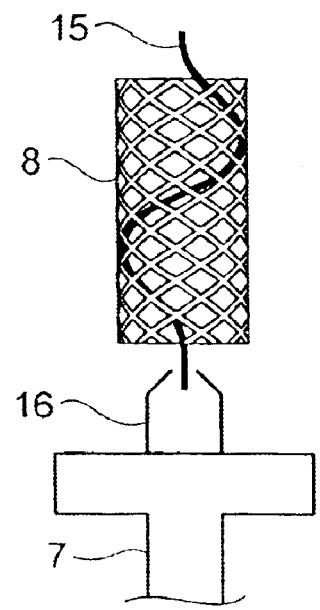
Figure 6C:
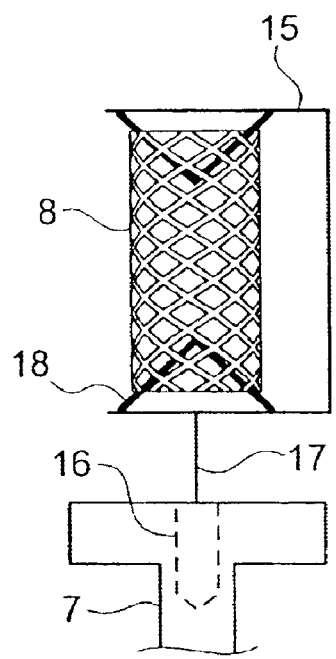
Figure 6D:
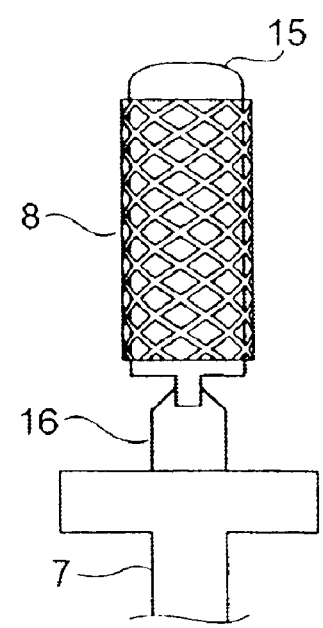

In the foregoing first embodiment, the stents are placed on rotating pins with upper portions that are shaped to directly receive the stents. Alternatively, in the first step of the present high-volume coating method process, the stents may be supplied for loading onto endless belt 1 already mounted on individual stent holders, where the upper portion of rotating pins 7 is adapted to grasp one end of the holder. FIG. 6 shows three example stent holder and cooperating rotating pin arrangements which are amenable to high-volume automated stent placement and removal operations. In FIG. 6a, stent 8 is mounted on stent holder 15. Stent holder 15 in turn is locked within a bayonet-type receiving portion 16 on top of rotating pin 7, where an extension 17 of stent holder 15 has been inserted into receiving portion 16 and rotated to lock the stent holder in place. Similarly, FIG. 6b illustrates another stent holder 15 formed from a nitinol wire that holds stent 8 by spring force at contact points on the stent's inner surface, where receiving portion 16 is a spring-loaded clamp that grasps one end of stent holder 15. FIG. 6c shows a further exemplary embodiment, wherein stent holder 15 is a wire frame with triangular ends 18, stent 8 is held under a light compressive force between the ends 18, and extension 17 from stent holder 15 is a wire that is placed into the receiving portion 16 of rotating pin 7 (in this case, a hole drilled into the top of pin 7). FIG. 6d shows another exemplary embodiment, wherein stent holder 15 is an inflatable balloon that lightly presses against the inner surface of stent 8 and is held, in this embodiment, in a receiving portion 16 that grasps one end of the stent holder balloon 15.

It should be understood that the foregoing description of various exemplary embodiments of possible stent holders and mating receiving mounts is not intended to be limiting, and a number of modifications and alternatives may be employed that would facilitate the performance of the present stent coating method at high production levels. Further, alternative coating and drying step arrangements may be employed, such as feeding the stents through multiple coating and drying cycles to apply a plurality of coats of coating material before the completed coated stent is removed from its stent holder, or conveying the stents through a plurality of coating sprayers spraying a plurality of different coatings, with or without drying periods between the coating layer applications.

Figure 7:
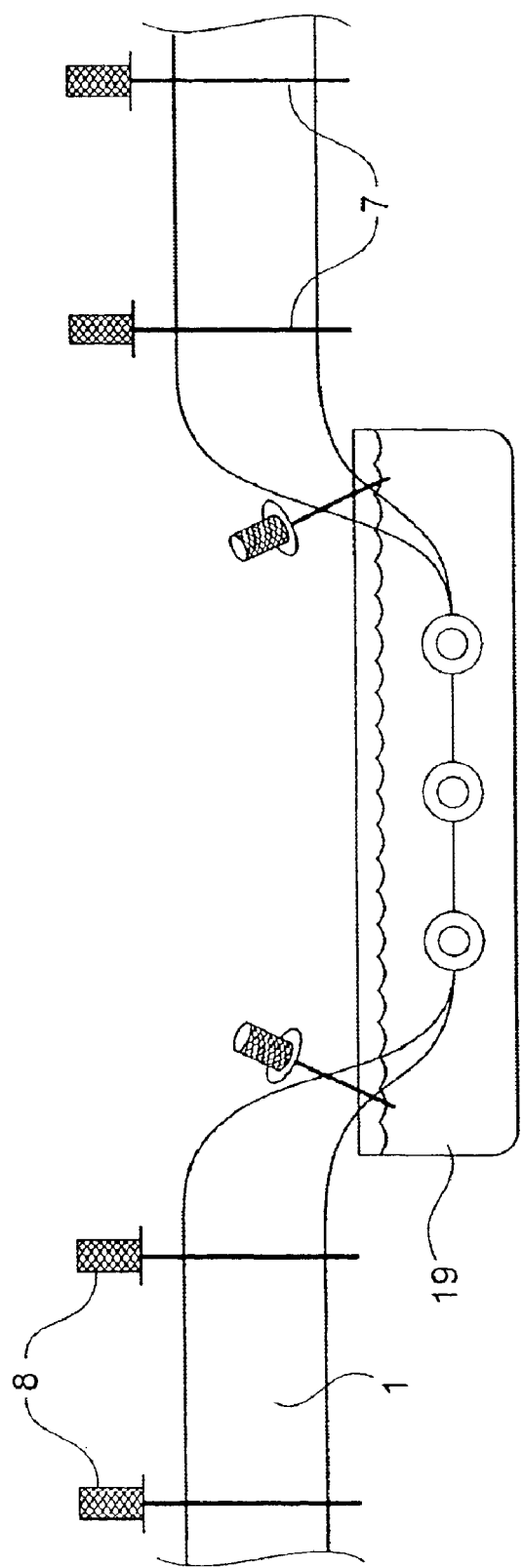
FIG. 7 is a schematic side view of the stent-bearing rotating pins and conveyer belt shown in FIG. 3 showing an alternative approach to the step of applying the stent coating by immersing the stents into a coating bath in accordance with the method of the present invention.

The foregoing alternative approaches to the stent placement step, which positively constrain stents 8 to remain mounted on rotating pins 7, facilitate a further embodiment of the present method. In this embodiment, rather than performing the step of applying the stent coating by using a stent coating sprayer, the coating may be applied by advancing endless belt 1 through a stent coating bath 19, as schematically illustrated in FIG. 7. It should be apparent to those of skill in the art that while positive control of rolling stents 8 on the top of rotating pins 7 is not a necessary prerequisite to use of a coating bath, use of the foregoing alternative stent holders coupled to the rotating pins enhances the control of the stents as they pass through coating bath 19. It should be further noted that while endless belt 1 is shown in FIG. 7 as being turned to a horizontal position to pass through coating bath 19, no orientation limitations are intended to be implied by the foregoing description, as a number of modifications and equivalent alternative arrangements are possible. For example, endless belt 1 may be arranged above the coating bath and located such that stents 8 are held and rotated about their longitudinal axes below belt 1, such that only the stents and their holders pass through the coating bath during the coating application step.

The term "therapeutic agent" as used herein includes one or more "therapeutic agents" or "drugs." The terms "therapeutic agents" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and antiangiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/ antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules or interfering RNA sequences. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. A method for coating stents, comprising the steps of:
    placing a stent on a stent holder, wherein the stent holder is attached to a conveyer;
    rotating the stent holder while the conveyer moves the stent through a stent coater; and
    applying a coating to the rotating stent as it passes through the stent coater.

2. The method of coating stents of claim 1, wherein the conveyer is an endless belt.

3. A method for coating stents, comprising the steps of:
    placing a plurality of stents on a plurality of stent holders, wherein the stent holders are attached to a conveyer;
    rotating the stent holders while the conveyer moves the stents through a stent coater; and applying a coating to the rotating stents while passing through the stent coater.

4. The method of coating stents of claim 3, wherein one of the plurality of stents is placed on each of the plurality of stent holders.

5. The method of coating stents of claim 4, wherein the conveyer is an endless belt, and the endless belt is moving as the plurality of stents is placed on the plurality of stent holders.

6. The method of coating stents of claim 5, wherein the stent coater includes a coating sprayer, and the conveyer moves the plurality of stents through a coating spray released from the coating sprayer.

7. The method of coating stents of claim 6, wherein the step of applying a coating further comprises:
    passing the stents through the coating spray at a first distance from the sprayer, then passing the stents through the coating spray at a distance from the sprayer greater than the first distance.

8. The method of coating stents of claim 6, wherein the step of applying a coating further comprises:
    passing the stents through the coating spray at a first distance from the sprayer, then
    passing the stents through the coating spray at a distance from the sprayer smaller than the first distance.

9. The method of coating stents of claim 6, wherein the endless belt is arranged such that after each of the plurality of stents passes through the coating spray at a first distance from the sprayer, the stents pass through the coating spray at least twice at distances from the sprayer greater than the first distance.

10. The method of coating stents of claim 6, wherein the endless belt is arranged such that after each of the plurality of stents passes through the coating spray at a first distance from the sprayer, the stents pass through the coating spray at least twice at distances from the sprayer smaller than the first distance.

11. The method of coating stents of claim 6, wherein
    the stent holders are rolling pins,
    the rolling pins are sized to permit stent placement over at least a portion of the pins.

12. The method of coating stents of claim 6, wherein the stent holders are rotating bases adapted to receive individual stent handling devices on which at least one stent is pre-mounted, and wherein the step of placing the stents on the stent holders further comprises:
    placing stents pre-mounted on stent handling devices onto the stent holders by engaging the stent handling devices with the rotating bases.

13. The method of coating stents of claim 6, wherein the coating sprayer sprays the stent coating toward the stents from a plurality of directions.

14. The method of coating stents of claim 6, wherein the coating sprayer rotates around the stents as stent coating is sprayed toward the stents.

15. The method of coating stents of claim 6, further comprising the step of:
    drying the coated stents prior to removal of the coated stents from the stent holders.

16. The method of coating stents of claim 15, wherein the drying step includes exposing the coated stents to a coating dryer prior to removal of the coated stents from the stent holders.

17. The method of coating stents of claim 15, wherein the conveyer is headed to accelerate coating drying.

18. The method of coating stents of claim 15, wherein the coating and drying steps are repeated a plurality of times before the coated stents are removed from the stent holders.

19. The method of coating stents of claim 5, wherein the stent coater includes a coating bath, and the conveyer moves the plurality of stents through the coating bath.

20. The method of coating stents of claim 5, wherein the step of placing at least one of the plurality of stents on the plurality of stent holders further is performed with an automated stent loader.

21. The method of coating stents of claim 20, further comprising the step of:
    removing the stents from the stent holders with an automated stent unloader.

* * * * *